US008921054B2

(12) United States Patent
Fallon

(10) Patent No.: US 8,921,054 B2
(45) Date of Patent: Dec. 30, 2014

(54) METHODS FOR DIAGNOSING PERVASIVE DEVELOPMENT DISORDERS, DYSAUTONOMIA AND OTHER NEUROLOGICAL CONDITIONS

(71) Applicant: Curemark, LLC, Rye, NY (US)

(72) Inventor: Joan M. Fallon, Bronxville, NY (US)

(73) Assignee: Curemark, LLC, Rye, NY (US)

( * ) Notice: Subject to any disclaimer, the term of this patent is extended or adjusted under 35 U.S.C. 154(b) by 0 days.

(21) Appl. No.: 14/037,652

(22) Filed: Sep. 26, 2013

(65) Prior Publication Data

US 2014/0170637 A1  Jun. 19, 2014

Related U.S. Application Data

(62) Division of application No. 13/208,963, filed on Aug. 12, 2011, now Pat. No. 8,580,522, which is a division of application No. 09/990,909, filed on Nov. 16, 2001, now Pat. No. 8,030,002.

(60) Provisional application No. 60/249,239, filed on Nov. 16, 2000.

(51) Int. Cl.
| | | |
|---|---|---|
| G01N 33/53 | (2006.01) | |
| G01N 33/567 | (2006.01) | |
| G01N 33/569 | (2006.01) | |
| C12Q 1/68 | (2006.01) | |

(52) U.S. Cl.
CPC ........ G01N 33/56983 (2013.01); C12Q 1/6883 (2013.01); C12Q 1/689 (2013.01); C12Q 1/6893 (2013.01); C12Q 1/6895 (2013.01); G01N 33/569 (2013.01); G01N 33/56905 (2013.01); G01N 33/56911 (2013.01)
USPC ............................. 435/7.1; 435/7.2; 435/7.32

(58) Field of Classification Search
None
See application file for complete search history.

(56) References Cited

U.S. PATENT DOCUMENTS

| | | |
|---|---|---|
| 3,002,883 A | 10/1961 | Butt et al. |
| 3,223,594 A | 12/1965 | Serge |
| 3,322,626 A | 5/1967 | D'Argento |
| 3,357,894 A | 12/1967 | Jose et al. |
| 3,515,642 A | 6/1970 | Mima et al. |
| 3,574,819 A | 4/1971 | Gross et al. |
| 3,860,708 A | 1/1975 | Prout |
| 3,940,478 A | 2/1976 | Kurtz |
| 4,079,125 A | 3/1978 | Sipos |
| 4,145,410 A | 3/1979 | Sears |
| 4,241,046 A | 12/1980 | Papahadjopoulos et al. |
| 4,280,971 A | 7/1981 | Wischniewski et al. |
| 4,447,412 A | 5/1984 | Bilton |
| 4,456,544 A | 6/1984 | Lupova et al. |
| 4,826,679 A | 5/1989 | Roy |
| 5,190,775 A | 3/1993 | Klose |
| 5,250,418 A | 10/1993 | Moller et al. |
| 5,324,514 A | 6/1994 | Sipos |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |
| 5,750,104 A | 5/1998 | Sipos |
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,096,338 A | 8/2000 | Lacy et al. |
| 6,149,585 A | 11/2000 | Gray |

(Continued)

FOREIGN PATENT DOCUMENTS

| | | |
|---|---|---|
| CA | 2198317 A1 | 2/1997 |
| CA | 2263703 A1 | 8/1999 |

(Continued)

OTHER PUBLICATIONS

U.S. Appl. No. 14/296,091, filed Jun. 4, 2014, Fallon.
Cichoke. Celiac disease. The complete book of enzyme therapy. Penguin. New York, NY. 1999; 174-177.
International preliminary report on patentability dated Jul. 17, 2014 for PCT/US2013/020183.
Office action dated Jul. 7, 2014 for U.S. Appl. No. 12/535,676.
Office action dated Aug. 7, 2014 for U.S. Appl. No. 13/836,135.
U.S. Appl. No. 14/087,930, filed Nov. 22, 2013, Fallon et al.

(Continued)

*Primary Examiner* — Albert Navarro
(74) *Attorney, Agent, or Firm* — Wilson Sonsini Goodrich & Rosati, P.C.

(57) ABSTRACT

Methods for aiding in the diagnosis of disorders including, but not limited to, PDDs (Pervasive Development Disorders), Dysautonomic disorders, Parkinson's disease and SIDS (Sudden Infant Death Syndrome). In one aspect, a diagnosis method comprises analyzing a stool sample of an individual for the presence of a biological marker (or marker compound) comprising one or more pathogens, which provides an indication of whether the individual has, or can develop, a disorder including, but not limited to, a PDD, Dysautonomia, Parkinsons disease and SIDS. Preferably, the presence of one or more pathogens is determined using a stool immunoassay to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

8 Claims, 4 Drawing Sheets

(56) References Cited

U.S. PATENT DOCUMENTS

| | | |
|---|---|---|
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,613,918 B2 | 12/2013 | Fallon |
| 2001/0023360 A1 | 9/2001 | Nelson et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0090653 A1 | 7/2002 | Fallon |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0079594 A1 | 4/2005 | Marion |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0258599 A1 | 11/2006 | Childers |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0199448 A1 | 8/2008 | Ross et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0117180 A1 | 5/2009 | Ortenzi et al. |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon |

(56) References Cited

U.S. PATENT DOCUMENTS

| | | |
|---|---|---|
| 2012/0027848 A1 | 2/2012 | Fallon |
| 2012/0070504 A1 | 3/2012 | Fallon |
| 2012/0114562 A1 | 5/2012 | Fallon |
| 2012/0114626 A1 | 5/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2012/0258149 A1 | 10/2012 | Heil et al. |
| 2013/0059001 A1 | 3/2013 | Fallon |
| 2013/0095152 A1 | 4/2013 | Fallon et al. |
| 2013/0113129 A1 | 5/2013 | Fallon et al. |
| 2013/0195833 A1 | 8/2013 | Fallon |
| 2013/0202581 A1 | 8/2013 | Fallon et al. |
| 2013/0224172 A1 | 8/2013 | Fallon et al. |

FOREIGN PATENT DOCUMENTS

| | | |
|---|---|---|
| CN | 1031562 A | 3/1989 |
| CN | 1329923 A | 1/2002 |
| DE | 4332985 | 3/1995 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1335706 B1 | 4/2005 |
| EP | 1019072 B1 | 5/2005 |
| EP | 1604677 A1 | 12/2005 |
| EP | 1931317 B1 | 6/2008 |
| EP | 2258837 A1 | 12/2010 |
| GB | 669782 A | 4/1952 |
| GB | 2347742 A | 9/2000 |
| JP | 62230714 A | 10/1987 |
| JP | H 04-364119 A | 12/1992 |
| WO | WO 84/02846 A1 | 8/1984 |
| WO | WO 90/02562 A1 | 3/1990 |
| WO | WO 94/19005 A1 | 9/1994 |
| WO | WO 95/22344 A1 | 8/1995 |
| WO | WO 97/32480 A1 | 9/1997 |
| WO | WO 98/22499 A2 | 5/1998 |
| WO | WO 98/22499 A3 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 00/21504 A1 | 4/2000 |
| WO | WO 01/27612 A2 | 4/2001 |
| WO | WO 01/43764 A2 | 6/2001 |
| WO | WO 01/45835 A1 | 6/2001 |
| WO | WO 01/27612 A3 | 10/2001 |
| WO | WO 01/43764 A3 | 11/2001 |
| WO | WO 02/14537 A2 | 2/2002 |
| WO | WO 02/14537 A3 | 5/2002 |
| WO | WO 02/051352 A2 | 7/2002 |
| WO | WO 03/051345 A2 | 6/2003 |
| WO | WO 03/059088 A1 | 7/2003 |
| WO | WO 2004/060074 A1 | 7/2004 |
| WO | WO 2005/115445 A1 | 12/2005 |
| WO | WO 2006/031554 A2 | 3/2006 |
| WO | WO 2006/044529 A1 | 4/2006 |
| WO | WO 2006/031554 A3 | 9/2006 |
| WO | WO 2007/002572 A2 | 1/2007 |
| WO | WO 2007/147714 A1 | 12/2007 |
| WO | WO 2008/021987 A2 | 2/2008 |
| WO | WO 2008/102264 A2 | 8/2008 |
| WO | WO 2009/114757 A2 | 9/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2010/120781 A1 | 10/2010 |
| WO | WO 2011/000924 A1 | 1/2011 |

OTHER PUBLICATIONS

Digestive Enzyme Preparation: Pancreatin listed in Japanese Pharmacopoeia, Aug. 2008, <URL:http://database.japic.or.jp/pdf/newPINS/00009938.pdf> (in Japanese with English translation).
Lebenthal, et al. Enzyme therapy for pancreatic insufficiency: present status and future needs. Pancreas. Jan. 1994;9(1):1-12.
MacDonald. Thyrotoxicosis treated with pancreatic extract and iodine. Lancet. 1943;244(6251):788.
Notice of allowance date Jan. 2, 2014 for U.S. Appl. No. 13/204,881.
Office action dated Jan. 15, 2014 for U.S. Appl. No. 13/836,135.
Office action dated Jan. 16, 2014 for U.S. Appl. No. 12/046,252.
Office action dated Jan. 24, 2014 for U.S. Appl. No. 12/054,343.
Office action dated Jan. 24, 2014 for U.S. Appl. No. 12/786,739.
Office action dated Mar. 11, 2014 for U.S. Appl. No. 11/533,818.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 16, 2013 for U.S. Appl. No. 12/535,676.
Okahata, et al. Lipid-coated enzymes as efficient catalysts in organic media. Trends in Biotechnology. 1997; 15(2):50-54.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Childhood Autism Rating Scale (CARS), Wikipedia, downloaded May 5, 2014.
Cichoke, Influenza. In: The Complete Book of Enzyme Therapy. D. Stewart, ed. Copyright 1999. Anthony J. Cichoke. Penquin Putnam, Inc., New York, New York. pp. "Contents", 50, 273-275 and 455.
Curemark press release. Curemark Receives Investigational New Drug Clearance For CM-AT For Autism. Mar. 26, 2009. http://www.medicalnewstoday.com/releases/143723.php.
Fido, et al. Olanzapine in the treatment of behavioral problems associated with autism: an open-label trial in Kuwait. Med Prime Pract. 2008;17(5):415-8. doi:10.1159/000141508. Epub Aug. 6, 2008.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Notice of allowance dated Jun. 12, 2014 for U.S. Appl. No. 13/448,061.
Office action dated Apr. 10, 2014 for U.S. Appl. No. 13/502,989.
Office action dated Apr. 16, 2014 for U.S. Appl. No. 13/705,763.
Office action dated May 12, 2014 for U.S. Appl. No. 13/733,873.
Office action dated May 13, 2014 for U.S. Appl. No. 13/313,629.
Office action dated May 15, 2014 for U.S. Appl. No. 13/488,061.
Office action dated May 16, 2014 for U.S. Appl. No. 13/313,708.
Office action dated Jun. 17, 2014 for U.S. Appl. No. 13/757,412.
Office action dated Jun. 17, 2014 for U.S. Appl. No. 13/737,225.
Office action dated Jun. 19, 2014 for U.S. Appl. No. 12/386,051.
Office action dated Jun. 27, 2014 for U.S. Appl. No. 14/007,793.
Pancreatin 8X USP Powder. Product Specification. Jul. 2000. In: Product Manual. American Laboratories Incorporated. Omaha, NE. p. 1.
Williams, et al. Intravenous secretin for autism spectrum disorders (ASD). Cochrane Database Syst Rev. Apr. 18, 2012;4:CD003495. doi: 10.1002/14651858.CD003495.pub3.
U.S. Appl. No. 13/503,844, filed Apr. 24, 2012, Fallon et al.
U.S. Appl. No. 13/836,135, filed Mar. 15, 2013, Fallon et al.
U.S. Appl. No. 13/926,822, filed Jun. 25, 2013, Fallon.
U.S. Appl. No. 14/007,793, filed Sep. 26, 2013, Fallon.
U.S. Appl. No. 14/037,696, filed Sep. 26, 2013, Fallon.
Adams, "Summary of Defeat Autism Now! (DNN!) Oct. 2001 Conference," retrieved from the internet Dec. 18, 2008, http://puterakembara.org/rm/DAN2001.htm.
Advisory Action dated Jun. 3, 2008 for U.S. Appl. No. 10/681,018.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.

(56) References Cited

OTHER PUBLICATIONS

Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
Arribas, et al. A Comparative study of the chymotrypsin-like activity of the rat liver multicatalytic proteinase and ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Austic, Development and adaptation of protein digestion. J Nutr. May 1985;115(5):686-97.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder, 2000: 1-3.

Axelrod. Secretin Treatment for Gastrointestinal Dysmobility in Patients with Familial Dysautonomia. New York University School of Medicine, Grant Precipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Barlow. A comparison of the blood pressure, kidney volume and the pancreatic secretory response following the vein administration of various secretin preparations. Am J Phys. 1927;81:182-188.
Beilmann, et al. Neoexpression of the c-met/hepatocyte growth factor-scatter factor receptor gene in activated monocytes. Blood. Dec. 1, 1997;90(11):4450-8.
Belmonte et al. Fragile X syndrome and autism at the intersection of genetic and neural networks. Nat Neurosci. Oct. 2006; 9(10):1221-5 (abstract only).
Blackmer. Parkinson disease: treatment and medication. Mar. 10, 2009., retrieved from the internet on Sep. 15, 2009, http://emedicine.medscape.com/article/312519-treatment.
Bode et al. Usefulness of a simple photometric determination of chymotrypsin activity in stools—results of a multicentre study. Clin Biochem, 1986; 19:333-37.
Borowitz, et al. Use of pancreatic enzyme supplements for patients with cystic fibrosis in the context of fibrosing colonopathy. Consensus Committee. J Pediatr. Nov. 1995;127(5):681-4.
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989; 86(23):9446-50.
Bray, et al. Effect of dietary protein content on weight gain, energy expenditure, and body composition during overating. A randomized controlled trial. JAMA. Jan. 4, 2012; 307(1):47-55.
Brudnak et al. Enzyme-based therapy for autism spectrum disorders—is it worth another look? Med Hypoth. 2002; 58:422-428.
Bruhat, et al. Amino acid limitation induces expression on CHOP, a CCAAT/enhancer binding protein-related gene, at both transcriptional and post-transcriptional levels. J Biol Chem. Jul. 11, 1997;272(28):17588-93.
Campbell et al. A genetic variant that disrupts MET transcription is associated with autism. Proc Natl Acad Sci USA. 2006; 103(45):16834-16839.
Carlton. Autism and malnutrition: the milk connection. Retrieved from the internet on Feb. 18, 2008, http://www.mercola.com/2004/autism_malnutrition.htm.
Carroccio, et al. Secondary impairment of pancreatic function as a cause of severe malabsorption in intestinal giardiasis: a case report. Am J Trop Med Hyg. Jun. 1997;56(6):599-602.
Carraccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
Chen, et al. Identification of two lysosomal membrane glycoproteins. J Cell Biol. Jul. 1985;101(1):85-95.
Chen, et al. Medicinal Functions of Bromelain and Its Application Prospect in Animal Husbandry. China Animal Husbandry & Veterinary Medicine, 2005; vol. 32, No. 1, p. 14-16. (in Chinese with English translation).
Cichoke, et al. The complete book of enzyme therapy. Penguin. 1998: 39, 42, 47, 50, and 53.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Craig, et al. Heat shock proteins: molecular chaperones of protein biogenesis. Microbiol Rev. Jun. 1993;57(2):402-14.

(56) References Cited

OTHER PUBLICATIONS

Croonenberghs, et al. Peripheral markers of serotonergic and noradrenergic function in post-pubertal, caucasian males with autistic disorder. Neuropsychopharmacology. Mar. 2000;22(3):275-83.

Cruse et al. Illustrated dictionary of immunology. CRC Press, New York. 1995.

Dajcs, et al. Lysostaphin is effective in treating methicillin-resistant *Staphylococcus aureus* endophthalmitis in the rabbit. Curr Eye Res. Jun. 2001;22(6):451-7.

Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.

Derwent. English abstract for RU 2286785 Nov. 10, 2006. Downloaded from the Derwent file Jul. 13, 2011.

Digestive Enzyme Wikipedia. Retrieved from the internet Sep. 10, 2009, http://en.wikipedia.org/wiki/Digestive_enzyme.

Dobbs et al. Link between *Helicobacter pylori* infection and idiopathic parkinsonism. Medical Hypothsis. 2000; 55(2):93-98.

Dockter et al. Determination of chymotrypsin in the feces by a new photometric method. Padiatr Padol. 1985; 20(3):257-265.

Dupiereux, et al. Creutzfeldt-jakob, Parkinson, lewy body dementia and Alzheimer diseases: from diagnosis to therapy. Cent Nerv Syst Agents Med Chem. Mar. 2009;9(1):2-11.

Edelson, et al. 3-Cyclohexene-1-glycine, an Isoleucine Antagonist. J. Am. Chem. Soc. 1958; 80(11):2698-2700.

Elkashef, et al. Biological markers of cocaine addiction: implications for medications development. Addict Biol. Jun. 2003;8(2):123-39.

Etheridge, et al. Acute pancreatitis results in induction of heat shock proteins 70 and 27 and heat shock factor-1. Pancreas. Oct. 2000;21(3):248-56.

Fapournoux, et al. Amino acid regulation of gene expression. Biochem J. Oct. 1, 2000;351(Pt. 1):1-12.

Fallingborg, et al. Measurement of gastrointestinal pH and regional transit times in normal children. J Pediatr Gastroenterol Nutr. Aug. 1990;11(2):211-4.

Fallon. Could one of the most widely prescribed antibiotics amoxicillin/clavulanate "augmentin" be a risk factor for autism? Med Hypotheses. 2005:64(2):312-5.

Ferrone, et al. Pancreatic enzyme pharmacotherapy. Pharmacotherapy. 2007; 27:910-920.

Filipek et al. The screening and diagnosis of autistic spectrum disorders. J. of Autism and Dev Disorders. 1999; 29(6).

Final Office Action dated Jan. 3, 2012 for U.S. Appl. No. 10/681,018.

Final Office Action dated Jan. 26, 2012 for U.S. Appl. No. 12/487,864.

Final Office Action dated Nov. 8, 2011 for U.S. Appl. No. 12/054,343.

Final Office Action dated Nov. 8, 2011 for U.S. Appl. No. 12/786,739.

Final Office Action dated Nov. 9, 2010 for U.S. Appl. No. 09/990,909.

Final Office Action dated Feb. 14, 2011 for U.S. Appl. No. 12/049,613.

Final Office Action dated Feb. 27, 2009 for U.S. Appl. No. 11/555,697.

Final Office Action dated Mar. 13, 2009 for U.S. Appl. No. 11/232,180.

Final Office Action dated Mar. 17, 2008 for U.S. Appl. No. 10/681,018.

Final Office Action dated Apr. 28, 2009 for U.S. Appl. No. 10/681,018.

Final Office Action dated May 11, 2010 for U.S. Appl. No. 11/555,697.

Final Office Action dated Jun. 25, 2008 for U.S. Appl. No. 11/213,255.

Final Office Action dated Jul. 2, 2010 for U.S. Appl. No. 12/046,252.

Final Office Action dated Jul. 27, 2004 for U.S. Appl. No. 09/990,909.

Finegold et al. Gastrointestinal microflora studies in late-onset autism. Clinical Infectious Diseases. 2002; 35(1):S6-S15.

Fitzsimmons, et al. High-dose pancreatic-enzyme supplements and fibrosing colonopathy in children with cystic fibrosis. N Engl J Med. May 1, 1997;336(18):1283-9.

Garcia et al. Detection of giardia lamblia, entamoeba histolytica/entamoeba dispar, and cryptosporidiam parvum antigens in human fecal specimens using the triage parasite panel enzyme immunoassay. Am Soc for Microbiology. 2000; 38(9):3337-3340.

Gardner. Absorption of intact peptides: studies on transport of protein digests and dipeptides across rat small intestine in vitro. Q J Exp Physiol. Oct. 1982;67(4):629-37.

Garner Jr. et al. Porcine Pancreatic Lipase—A Glycoprotein, J Biol Chem. Jan. 25, 1972;247(2):561-5.

Giglio, et al. Failure to thrive: the earliest feature of cystic fibrosis in infants diagnosed by neonatal screening. Acta Paediatr. Nov. 1997;86(11):1162-5.

Goff, et al. Production of abnormal proteins in *E. coli* stimulates transcription of Ion and other heat shock genes. Cell. Jun. 1985;41(2):587-95.

Green, et al. Amino-terminal polymorphisms of the human beta 2-adrenergic receptor impart distinct agonist-promoted regulatory properties. Biochemistry. Aug. 16, 1994;33(32):9414-9.

Gupta, et al. Th1- and Th2-like cytokines in CD4 and CD8+ T cells in autism. J Neuroimmunol. May 1, 1998;85(1):106-9.

Hadjivassiliou, et al. Does cryptic gluten sensitivity play a part in neurological illness? Lancet. Feb. 10, 1996;347(8998):369-71.

Happe et al. The neuropsychology of autism. Brain. 1996; 119:1377-1400.

Happe et al. Time to give up on a simple explanation for autism. Nat Neurosci. Oct. 2006: 9(10):1218-20.

Heijerman, et al. Omeprazole enhances the efficacy of pancreatin (pancrease) in cystic fibrosis. Ann Intern Med. Feb. 1, 1991;114(3):200-1.

Hendren et al. Mechanistic biomarkers for autism treatment. Medical Hypotheses. 2009; 73:950-954.

Horvath et al. Improved social and language skills after secretin administration in patients with autistic spectrum disorders. Journal of the Association for Academic Minority Physicians. Jan. 1998; 9(1):9-15.

Horvath, et al. Autism and gastrointestinal symptoms. Curr Gastroenterol Rep. Jun. 2002;4(3):251-8.

Horvath, et al. Gastrointestinal abnormalities in children with autistic disorder. J Pediatr. Nov. 1999:135(5):559-63.

Hoshiko et al. The effect of the gastrointestinal hormones on colonic muscosal blood flow. Acta Medica Nagasakiensia. 1994; 39(4):125-130.

Huang, et al. Apoptotic cell death in mouse models of GM2 gangliosidosis and observations on human Tay-Sachs and Sandhoff diseases. Hum Mol Genet. Oct. 1997;6(11):1879-85.

Huang, et al. Mapping of the human APOB gene to chromosome 2p and demonstration of a two-allele restriction fragment length polymorphism. Proc Natl Acad Sci U S A. Feb. 1986;83(3):644-8.

Information of Papain from Worthington Enzymes webpage http://www.worthington-biochem.com/pap/default.html Downloaded Jan. 17, 2013.

International search report and written opinion dated Feb. 21, 2013 for PCT/US2013/020183.

International search report and written opinion dated Jan. 18, 2011 for PCT/US2010/057341.

International search report and written opinion dated Nov. 12, 2012 for PCT/US2012/034489.

International search report and written opinion dated Feb. 15, 2011 for PCT/US2010/053484.

International search report and written opinion dated Mar. 2, 2010 for PCT/US2010/020253.

International search report and written opinion dated Jun. 9, 2010 for PCT/US2010/030895.

International search report and written opinion dated Sep. 25, 2009 for PCT/US2009/049374.

International search report and written opinion dated Mar. 5, 2010 for PCT/US2010/020259.

(56) References Cited

OTHER PUBLICATIONS

International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
Jenkins, et al. Management of gastroenteritis. Archives of Disease in Childhood. 1990; 65:939-941.
Juhl. Fibromyalgia and the serotonin pathway. Altern Med Rev. 1998; 3(5):367-375.
Kachrimanis, et al. Tensile strength and disintegration of tableted silicified microcrystalline cellulose: influences of interparticle bonding. J Pharm Sci. Jul. 2003;92(7):1489-501.
Kaspar et al. New photometric assay for chymotrypsin in stool. Clinical Chemistry, 1984;30(11):1753-1757.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koster et al. Evidence based medicine and extradigestive manifestations of *Helocobacter pylori*. Acta Gastro-Enterologica Belgica. 2000; 63(4):388-392.
Lashkari, et al. Williams-Beuren syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Levy, et al. Relationship of dietary intake to gastrointestinal symptoms in children with autistic spectrum disorders. Biol Psychiatry. Feb. 15, 2007;61(4):492-7.
Lieberman. Pharmaceutical Dosage Forms. vol. 2: Disperse Systems, New York Marcel Dekker, Inc. 1996; 243-258.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacReady. Parkinson's Disease Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(10):1-27.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988: 419(1):704-707. (in Polish with English abstract/summary).
Marsh. Neuropsychiatric aspects of parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
Medsafe. Data sheet for alpha-lactose, Jul. 21, 2008, http://www.medsafe.govt.nz/Profs/Datasheet/a/Alphalactulosesyrup.htm.
Melmed, et al. Metabolic markers and gastrointestinal symptoms in children with autism and related disorders. J Pediatr Gast Nutr. 2000; 31:S31-S32. Abstract only.
Merck. Autism. Merck manual online medical library home addition, retrieved from the internet Mar. 10, 2008, http://www.merel.com/mmhge/sec23/ch286/ch286b.html.
MeSH browser. "Child Development Disorders, Pervasive," and "Attention deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michell et al. Biomarkers and parkinson's disease. Brain. 2004; 127(8):1693-1705.
Millipore EMD catalog (online). Papain, unit definition, EMD Millipore Corp, 2013, Downloaded May 13, 2013.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopepridases in the blood pressure regulation. Biological and Pharmaceutical Bulletin of Japan, Pharmaceutical Sociey of Japan. 2004; 27(6):768-771.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56 ,58, 60, 64.
Neuer, et al. The role of heat shock proteins in reproduction. Hum Reprod Update. Mar.-Apr. 2000;6(2):149-59.
Nevo et al. Acute immune polyneuropathies: correlations of serum antibodies to *Campylobacter jejuni* and *Helicobacter pylori* with anti-gm antibodies and clinical patterns of disease. J of Inf diseases. 1997; 175(S2):S154-6.
NINDS Dysautonimia Information Page, retrieved from the internet Sep. 10, 2009, http://www.ninds.nih.gov/disorders/dysautonomia/dysautonomia.htm.
NINDS Guillain-Barre Syndrome Information Page, retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Allowance dated Feb. 17, 2012 for U.S. Appl. No. 10/681,018.
Notice of Allowance dated Mar. 21, 2012 for U.S. Appl. No. 12/487,864.
Notice of Allowance dated Apr. 15, 2011 for U.S. Appl. No. 12/487,868.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of Allowance dated Jun. 27, 2011 for U.S. Appl. No. 12/238,415.

(56) References Cited

OTHER PUBLICATIONS

Notice of Allowance dated Jun. 28, 2011 for U.S. Appl. No. 12/487,868.
Notice of Allowance dated Jun. 30, 2011 for U.S. Appl. No. 09/990,909.
Notice of allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of Allowance dated Sep. 20, 2011 for U.S. Appl. No. 12/283,090.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
Office action dated Jan. 12, 2012 for U.S. Appl. No. 12/047,818.
Office action dated Jan. 22, 2013 for U.S. Appl. No. 13/562,999.
Office action dated Jan. 25, 2013 for U.S. Appl. No. 13/208,963.
Office Action dated Feb. 1, 2012 for U.S. Appl. No. 12/493,122.
Office action dated Feb. 14, 2013 for U.S. Appl. No. 13/193,346.
Office action dated Feb. 14, 2013 for U.S. Appl. No. 13/407,408.
Office action dated Feb. 21, 2013 for U.S. Appl. No. 12/047,818.
Office Action dated Mar. 5, 2012 for U.S. Appl. No. 12/535,676.
Office action dated Mar. 5, 2013 for U.S. Appl. No. 12/493,122.
Office Action dated Mar. 19, 2012 for U.S. Appl. No. 13/204,881.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office Action dated Apr. 5, 2012 for U.S. Appl. No. 11/555,697.
Office Action dated Apr. 9, 2012 for U.S. Appl. No. 13/208,963.
Office Action dated Apr. 27, 2011 for U.S. Appl. No. 10/681,018.
Office Action dated Apr. 28, 2011 for U.S. Appl. No. 12/283,090.
Office action dated May 9, 2013 for U.S. Appl. No. 13/204,881.
Office action dated May 15, 2013 for U.S. Appl. No. 13/502,989.
Office Action dated May 24, 2011 for U.S. Appl. No. 12/487,864.
Office action dated Jun. 13, 2012 for U.S. Appl. No. 12/493,122.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 29, 2011 for U.S. Appl. No. 11/555,697.
Office action dated Jul. 11, 2012 for U.S. Appl. No. 12/573,353.
Office action dated Jul. 18, 2012 for U.S. Appl. No. 12/047,818.
Office action dated Aug. 13, 2012 for U.S. Appl. No. 13/208,963.
Office action dated Sep. 13, 2012 for U.S. Appl. No. 13/481,087.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 25, 2012 for U.S. Appl. No. 13/144,286.
Office action dated Oct. 25, 2012 for U.S. Appl. No. 13/144,290.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office action dated Dec. 6, 2012 for U.S. Appl. No. 13/002,136.
Office action dated Dec. 15, 2011 for U.S. Appl. No. 12/493,147.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Olivar-Parra, et al. Training referential communicative skills to individuals with autism spectrum disorder: a pilot study. Psychological Reports. 2011; 109:921-939.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.
Patel, et al. Formulation and evaluation of mucoadhesive glipizide microspheres. AAPS PharmSciTech. 2005; 6(1):E49-E55.
Perman et al. Role of ph in production of hydrogen from carbohydrates by colonic bacterial flora. J Clin Invest. 1981; 24(4):684-685.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Remtulla et al. Stool chymotrypisn activity measured by a spectrophotometric procedure to identify pancreat disease in infants. Clinical Biochemistry. Dec. 1986;19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.

(56) References Cited

OTHER PUBLICATIONS

Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Rider, et al. Perspective of biochemical research in the neuronal ceroid-lipofuscinosis Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lyosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Sabra, et al. Linkage ileal-lymphoid-nodular hyperplasia (ILNH), food allergy and CNS developmental: evidence for a non-IgE association. Ann Aller Asth Immunol. 1999; 82(1):81. Abstract only.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schumann. Medical, nutritional and technological properties of lactulose. An update. Eur J Nutr. Nov. 2002;41 Suppl 1:I17-25.
Seneca et al. Enhancement of brain l-dopa concetration with a-chymotrypsm. J American Geriatrics Society. 1973;256-258. Abstract only.
Serna, et al. Pathogenesis and treatment of Shiga toxin-producing *Escherichia coli* infections. Curr Opin Gastroenterol. Jan. 2008;24(1):38-47.
Sherwood et al. A new class of high-functionality excipients: silicified microcrystalline cellulose. Pharm Tech. 1998; 22(10):78-88.
Sillanaukee, et al. Improved diagnostic classification of alcohol abusers by combining carbohydrate-deficient transferrin and gamma-glutamyltransferase. Clin Chem. Apr. 2001;47(4):681-5.
Singh, et al. Plasma increase of interleukin-12 and interferon-gamma. Pathological significance in autism. J Neuroimmunol. May 1996;6691-2):143-5.
Skeels et al. Crytosporidium infection in Oregon public health clinic patients 1985-88: the value of statewide laboratory surveillance. AJPH. 1990; 80(3):305-308.
Smith, et al. Fecal chymotrypsin and trypsin determinations. Canadian Medical Association Journal. 1971; 104(8):691-4 and 697.
Stein, et al. Nitrogen metabolism in normal hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997. Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Strader, et al. Structural basis β-adrenergic receptor function. FASEB J. May 1989;3(7):1825-32.

Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
The Alzheimer's Association. Basics of Alzheimer's Disease. 2005, 32 pages. http://www.alz.org/national/documents/brochure_Basicsofalz_low/pdf.
Thefreedictionary. Term Sprinkles. Www.thefreedictionary.com. Accessed Nov. 2, 2011. 1 page.
Thomas, et al. Defective protein folding as a basis of human disease. Trends Biochem Sci. Nov. 1995;2091 1):456-9.
Tran, et al. Treatment of complex regional pain syndrome: a review of the evidence. Can J Anaesth. Feb. 2010;57(2):149-66.
Tsang et al. Extragastroduodenal conditions associated with *Heliobacter pylori* infection. Hong Kong Medical Journal. 1999; 5(2):169-174.
USDA. FDA Drug Safety Communication: *Clostridium difficile*-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Vilanova, et al. Preparative isolation of the two forms of pig pancreatic pro-(carboxypeptidase A) and their monomeric carboxypeptidases A. Biochem J. Aug. 1, 1985;229(3):605-9.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (PART 1) Dec. 1999;38(12 Suppl):32S-54S.
Vokmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (PART 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004;82:835-839.
Weintraub, et al. Morphometric studies of pancreatic acinar granule formation in NCTR-Balb/c mice. J Cell Sci. May 1992;102 ( Pt 1):141-7.
Wender et al. Prevalence of attention deficit disorder, residual type, and other psychiatric disorders in patients with irritable colon syndrome. Am J Psychiatry. 1983;140(12):1579-82 Abstract only.
Williams, et al. Eating habits of children with autism. Pediatr Nurs. May-Jun. 2000;26(3):259-64.
Wisniewski, et al. Therapeutic approaches for prion and Alzheimer's diseases. FEBS J. Aug. 2007;274(15):3784-98. Epub Jul. 6, 2007.
Wohlman et al. Enhancement of drug activity by chymotrypsin, penicillin penetration into granulomatous sesions and inflammatory fluids. Cellular and Molecular Life Sciences 1969; 25(9):953-954.
Woodward et al. Ischaemic enterocolitis complicating aidiopathic dysatuonomia. Gut. 1998; 43:285-287.
Youngberg, et al. Comparison of gastrointestinal pH in cystic fibrosis and healthy subjects. Dig Dis Sci. May 1987;32(5):472-80.
Yuan, et al. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;169(8):5483-90.

(56) References Cited

OTHER PUBLICATIONS

Zhang et al. Lactulose-mannitol intestinal permeability test in children with diarrhea caused by rotavirus abd cryptosporidium. J of Pediatric Gastro & Nutrition. 2000;31(1):16-21.
Borlongan, Recent preclinical evidence advancing cell therapy for Alzheimer's disease. Exp Neurol. Sep. 2012;237(1):142-6. doi:10.1016/j.expneurol.2012.06.024.Epub Jun. 27, 2012.
Carroccio, et al. Pancreatic enzyme therapy in childhood celiac disease. A double-blind prospective randomized study. Dig Dis Sci. Dec. 1995;40(12):2555-60.
Creon. Full prescribing information. Last edited Mar. 2013. Abbvie Inc. 2012. www.rxabbvie.com/pdf/creon_PI.pdf.
Eaves, et al. The criterion-related validity of the Childhood Autism Rating Scale and the Autism Behavior Checklist. J Abnorm Child Psychol. Oct. 1993;21(5):481-91. abstract only.
Evans, et al. Pancreatic insufficiency in adult celiac disease: do patients require long-term enzyme supplementation? Dig Dis Sci. Oct. 2010;55(10):2999-3004. doi:10.1007/s10620-010-1261-y. Epub May 11, 2010.
International search report and written opinion dated Aug. 27, 2013 for PCT/US2013/043444.
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Leeds, et al. Is exocrine pancreatic insufficiency in adult coeliac disease a cause of persisting symptoms? Aliment Pharmacol Ther. Feb. 1, 2007;25(3):265-71.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Oct. 29, 2013 for U.S. Appl. No. 13/204,881.
Office action dated Jul. 15, 2013 for U.S. Appl. No. 13/002,136.
Office action dated Jul. 31, 2013 for U.S. Appl. No. 13/757,412.
Office action dated Aug. 2, 2013 for U.S. Appl. No. 12/535,676.
Office action dated Aug. 14, 2013 for U.S. Appl. No. 13/448,061.
Office action dated Aug. 28, 2013 for U.S. Appl. No. 13/313,629.
Office action dated Sep. 9, 2013 for U.S. Appl. No. 13/502,989.
Office action dated Oct. 24, 2013 for U.S. Appl. No. 13/313,708.
Office action dated Nov. 29, 2013 for U.S. Appl. No. 13/193,346.
Pancrease. Patient information leaflet. Pancrease HL Capsules. Last updated Apr. 30, 2013. Janssen-cilag LTD. www.medicines.org.uk/EMC/medicine/7326.
Petrolatum: Pharmaceutical Excipients. London: Pharmaceutical Press. 2006. 1-6.
Sienaert, et al. Evidence-based treatment strategies for treatment-resistant bipolar depression: a systematic review. Bipolar Disord. Feb. 2013;15(1):61-9. doi:10.1111/bdi.12026. Epub Nov. 27, 2012.
Xu. Pancreatin therapy in chronic pancreatitis. Clin J Dig, May 2005; 25(5):313-315. (in Chinese with English translation).
Notice of allowance Aug. 11, 2014 for U.S. Appl. No. 13/193,346.

| CHILD 1 | + H. pylori |
| | + Giardia |
| | + Cryptosporidium |
| | |
| CHILD 2 | + Rotavirus |
| | + Cryptosporidium |
| | + H. pylori |
| | + Girdia |

FIG. 1

| PATIENT | H.pylori | Cryptosporidium | E.histolytica | Giardia | Rota/virus | Camphylobacter | C. difficile |
|---|---|---|---|---|---|---|---|
| Parkinson 1 | + | + | + | + | + | + | + |
| Parkinson 2 | + | + | + | + |  | + | + |
| Parkinson 3 | + |  |  | + | + | + |  |
| Parkinson 4 |  | + |  |  |  |  |  |
| Parkinson 5 | + | + |  |  | + |  |  |
| Parkinson 6 | + |  |  |  |  |  | + |
| Parkinson 7 | + |  | + | + |  |  |  |
| Parkinson 8 | + | + | + | + |  | + |  |
| Parkinson 9 |  | + |  | + | + | + | + |
| Parkinson 10 | + | + |  |  | + |  | + |
| Parkinson 11 | + |  |  |  | + |  | + |
| Parkinson 12 | + |  |  | + | + |  |  |
| Parkinson 13 |  | + | + | + |  | + |  |
| Parkinson 14 | + | + |  | + |  | + | + |
| Parkinson 15 | + | + |  |  | + | + |  |
|  |  |  |  |  |  |  |  |
| Non-P 1 |  |  |  |  |  |  |  |
| Non-P 2 |  |  |  |  |  |  |  |
| Non-P 3 |  |  |  |  |  |  |  |
| Non-P 4 |  |  |  |  |  |  |  |
| Non-P 5 |  |  |  |  |  |  |  |
| Non-P 6 |  |  |  | + |  |  |  |
| Non-P 7 |  |  |  |  |  |  |  |
| Non-P 8 |  |  |  |  |  |  |  |
| Non-P 9 |  |  |  |  |  |  |  |
| Non-P 10 |  |  |  |  |  |  |  |
| Non-P 11 |  |  |  |  |  |  |  |
| Non-P 12 | + |  |  |  |  |  |  |
| Non-P 13 |  |  |  |  |  |  |  |
| Non-P 14 |  |  |  |  |  |  |  |
| Non-P 15 |  |  |  |  |  |  |  |

FIG. 2

| PATIENT | Age | H.pylori | Cryptosporidium | E.histolytica | Giardia | Rotavirus | Camphylobacter | C.difficile |
|---|---|---|---|---|---|---|---|---|
| ADD 1 | 10 | + |  | + | + | + |  | + |
| ADD 2 | 6 | + | + |  |  |  |  | + |
| ADHD 3 | 9 |  |  | + |  | + | + |  |
| ADHD 4 | 6 |  | + | + | + |  | + |  |
| ADD 5 | 9 | + | + | + | + | + | + | + |
| ADD 6 | 11 |  | + |  |  |  | + |  |
| ADD 7 | 14 | + |  |  |  | + |  |  |
| ADHD 8 | 4 | + | + | + |  |  |  |  |
| ADD 9 | 16 |  | + | + | + | + | + |  |
| ADHD 10 | 12 |  | + | + |  |  |  | + |
| ADD 11 | 11 | + |  |  |  | + | + |  |
| ADD 12 | 7 |  | + |  | + | + |  | + |
| ADD 13 | 9 | + | + | + | + |  | + |  |
|  |  |  |  |  |  |  |  |  |
| Non-ADD 1 | 10 |  |  |  |  |  |  |  |
| Non-ADD 2 | 6 |  |  | + |  |  |  |  |
| Non-ADD 3 | 9 |  |  |  |  |  |  |  |
| Non-ADD 4 | 6 |  |  |  |  |  |  |  |
| Non-ADD 5 | 9 |  |  |  |  |  |  |  |
| Non-ADD 6 | 11 | + |  |  |  |  | + |  |
| Non-ADD 7 | 14 |  |  |  |  |  |  |  |
| Non-ADD 8 | 4 |  |  |  |  |  |  |  |
| Non-ADD 9 | 16 |  |  |  |  |  |  |  |
| Non-ADD 10 | 12 |  |  |  |  |  |  |  |
| Non-ADD 11 | 11 | + |  |  |  |  |  |  |
| Non-ADD 12 | 7 |  |  |  |  |  |  |  |
| Non-ADD 13 | 9 |  |  |  |  |  |  |  |
| Non-ADD 14 | 9 |  |  |  |  |  |  |  |

FIG. 3

| Patient | Giardia | Cryptosporidium | E.Histolytica | Adendovirus | Rotavirus | H.Pylori | Cyclospora | Mycrosporidia | IsosporaBelh |
|---|---|---|---|---|---|---|---|---|---|
| Autistic 1 | + | | | | | | | | |
| Autistic 2 | | + | | | | + | | | + |
| Autistic 3 | + | | | | | + | | | |
| Autistic 4 | | | | + | | + | | | |
| Autistic 5 | + | | | | | | | | |
| Autistic 6 | | + | | | + | | | | |
| Autistic 7 | + | | | | | + | | | |
| NonAutistic1 | | | | | | | | | |
| NonAutistic2 | | | | | | | | | |
| NonAutistic3 | | | | | | | | | |
| NonAutistic4 | | | | | | | | | |
| NonAutistic5 | | | | | | | | | |
| NonAutistic6 | | | | | | | | | |
| NonAutistic7 | | | | | | | | | |

FIG. 4

METHODS FOR DIAGNOSING PERVASIVE DEVELOPMENT DISORDERS, DYSAUTONOMIA AND OTHER NEUROLOGICAL CONDITIONS

CROSS REFERENCE TO RELATED APPLICATION

This application is a divisional patent application of U.S. Utility application Ser. No. 13/208,963, filed Aug. 12, 2011, now U.S. Pat. No. 8,580,522, which is a divisional patent application of U.S. Utility application Ser. No. 09/990,909, filed Nov. 16, 2001, now U.S. Pat. No. 8,030,002, which claims the benefit of U.S. Provisional Application No. 60/249,239, filed Nov. 16, 2000, each of which is herein incorporated by reference in its entirety.

TECHNICAL FIELD OF THE INVENTION

The present invention generally relates to methods for aiding in the diagnosis of disorders including, but not limited to, PDDs (Pervasive Development Disorders), Dysautonomic disorders, Parkinsons disease and SIDS (Sudden Infant Death Syndrome). More particularly, the invention relates to a diagnosis method comprising analyzing a stool sample of an individual for the presence of a biological marker (or marker compound) comprising one or more pathogens, which provides an indication of whether the individual has, or can develop, a disorder including, but not limited to, a PDD, a Dysautonomic disorder, Parkinson's disease or SIDS.

BACKGROUND

Currently, extensive research is being conducted to determine associations between gastrointestinal dysfunction and a variety of human disorders that, heretofore, have been of unknown etiology. For example, an association between dysautonomic conditions and gastrointestinal dysfunction has been described in U.S. patent application Ser. No. 09/929,592, filed on Aug. 14, 2001, entitled "Methods For Diagnosing and Treating Dysautonomia and Other Dysautonomic Conditions, which is commonly owned and fully incorporated herein by reference. Further, a relationship between gastrointestinal conditions and PDDs such as Autism, ADD (Attention Deficit Disorder) and ADHD (Attention Deficit Hyperactivity Disorder) has been described in detail in U.S. patent application Ser. No. 09/466,559, filed Dec. 17, 1999, entitled "Methods For Treating Pervasive Development Disorders," and U.S. Ser. No. 09/707,395, filed on Nov. 7, 2000, entitled "Methods For Treating Pervasive Development Disorders", both of which are commonly owned and incorporated herein by reference.

Based on these findings, it is thus desirable to continue research in finding biologic markers of gastrointestinal dysfunction that may aid in the diagnosis of certain diseases and disorders. For example, the effect of various pathogens on the gastrointestinal tract, and the association of such pathogens to disorders such as PDD and dysautonomia, has heretofore not been researched. Various microorganisms that are of interest will now be discussed.

*Helicobacter pylori* (*H. pylori*) is generally associated with chronic gastritis and peptic ulcer in children and adults. The prevalence of *H. pylori* is highest in developing countries and lowest in developed countries. Ethnicity, socioeconomic status, household crowding, and other conditions contribute to the formation of *H. pylori* infection. Infection is rarely symptomatic in children, and duodenal ulcers are generally not seen in children less than 10 years of age. Various diseases that are caused, or believed to be caused by *H. pylori* infection are known. For instance, it has been postulated that *H. pylori* plays a role in auto-immune athero-sclerosis.

Esophageal reflux disease (GORD) has further been postulated to be caused by *H. pylori* in a mechanism whereby somatostatin induces the hypothalamus to decrease the release of growth hormone from the pituitary affecting the adrenal control of cortisol. The change in cortisol ultimately affects the gastrin release mechanism causing an increase in acid.

*Cryptosporidium parvum* can be associated with infections of the gastrointestinal tract in children and in immunocompromised populations. It is generally thought to account for up to 20% of all cases of diarrhea in developing countries and potentially life threatening in children with AIDS due to the induction of severe malnutrition. These infections are generally asymptomatic and occur in tandem with other infections such as one with *Giardia*.

In 1993, a large outbreak of *Cryptosporidium parvum* occurred in Milwaukee Wis. in which 400,000 people were affected. It has a seasonal effect of being more prevalent in the late summer in children under the age of 15 years.

*Giardia lamblia* is a common cause of diarrhea in humans and other mammals throughout the world. In its most severe form, it has been found to cause infectious lymphocytosis. Although rare, infection with *Giardia* can be protracted and debilitating. *Giardia lamblia* is a flagellate that encysts, and generally does not cause symptomotology. However, when found in the trophozoite form, severe diarrhea can result. Symptoms can include diarrhea, vomiting, fatigue, and growth retardation in children. Malabsorption results from infection with the trophzoite form, and potential blockage of the microvilli of the intestines occurs. There may be an interaction between decreased levels of IgA in the gastrointestinal system and giardiasis.

*Clostridium* infections of the gastrointestinal tract are of the *perfringes, botulinum* and *difficele* varieties. Perfringens food poisoning is the term used to describe the common foodborne illness caused by *C. perfringens*. A more serious but rare illness is also caused by ingesting food contaminated with Type C strains. The latter illness is known as enteritis necroticans. The common form of *perfringens* poisoning is characterized by intense abdominal cramps and diarrhea which begin 8-22 hours after consumption of foods containing large numbers of those *C. perfringens* bacteria capable of producing the food poisoning toxin. The illness is usually over within 24 hours but less severe symptoms may persist in some individuals for 1 or 2 weeks. A few deaths have been reported as a result of dehydration and other complications. Necrotic enteritis caused by *C. perfringens* is often fatal. This disease also begins as a result of ingesting large numbers of the causative bacteria in contaminated foods. This disease is a food infection; only one episode has ever implied the possibility of intoxication (i.e., disease from preformed toxin).

*Clostridium difficile* is an infection generally caused by changes in the intestinal mucosa. Those changes are caused by an overuse of antibiotics creating an intestinal environment favorable to the infiltration with *Clostridium difficile*. Infection with *C. difficile* is generally debilitating and *C. difficile* is a gram-positive, spore forming, anaerobic bacillus which can produce toxin-mediated diarrhea or pseudomembranous colitis. It has been isolated from soil, sand, hay, and animal dung. *C. difficile* colonization of the colon occurs in 2%-3% of healthy adults. Following exposure to antibacterial agents, the rate of asymptomatic colonization in adults averages between 5% to 15%, but rates as high as 46% have been reported. Carriage rates of up to 70% have been reported in children below the age of one year, but by two years of age the "normal" colonic flora is established and the frequency of colonization decreases to that of healthy adults. Of interest is that healthy children less than one year of age are the only population in which *C. difficile* toxins are frequently detected in the stool in the absence of clinical symptoms. One suggestion advanced to explain this observation is that the infant's gut cannot respond to the toxin.

*Clostridium botulinum* is an anaerobic, spore-forming rod that produces a potent neurotoxin. The spores are heat-resistant and can survive in foods that are incorrectly or minimally processed. Seven types (A, B, C, D, E, F and G) of botulism are recognized, based on the antigenic specificity of the toxin produced by each strain. Types A, B, E and F cause human botulism. Types C and D cause most cases of botulism in animals. Animals most commonly affected are wild fowl and poultry, cattle, horses and some species of fish. Although type G has been isolated from soil in Argentina, no outbreaks involving it have been recognized. Foodborne botulism (as distinct from wound botulism and infant botulism) is a severe type of food poisoning caused by the ingestion of foods containing the potent neurotoxin formed during growth of the organism. The toxin is heat labile and can be destroyed if heated at 80° C. for 10 minutes or longer. The incidence of the disease is low, but the disease is of considerable concern because of its high mortality rate if not treated immediately and properly. Most of the 10 to 30 outbreaks that are reported annually in the United States are associated with inadequately processed, home-canned foods, but occasionally commercially produced foods have been involved in outbreaks. Sausages, meat products, canned vegetables and seafood products have been the most frequent vehicles for human botulism.

The life cycle of *Entamoeba histolytica* involves trophozoites (the feeding stage of the parasite) that live in the host's large intestine and cysts that are passed in the host's feces. Humans are infected by ingesting cysts, most often via food or water contaminated with human fecal material. The trophozoites can destroy the tissues that line the host's large intestine, so of the amoebae infecting the human gastrointestinal tract, *E. histolytica* is potentially the most pathogenic. In most infected humans the symptoms of "amoebiasis" (or "amebiasis") are intermittent and mild (various gastrointestinal upsets, including colitis and diarrhea). In more severe cases the gastrointestinal tract hemorrhages, resulting in dysentery. In some cases the trophozoites will enter the circulatory system and infect other organs, most often the liver (hepatic amoebiasis), or they may penetrate the gastrointestinal tract resulting in acute peritonitis; such cases are often fatal. As with most of the amoebae, infections of *E. histolytica* are often diagnosed by demonstrating cysts or trophozoites in a stool sample. Infections that sometimes last for years may be accompanied by no symptoms, vague gastrointestinal distress, and/or dysentery (with blood and mucus). Most infections occur in the digestive tract but other tissues may be invaded. Complications include ulcerative and abscess pain and, rarely, intestinal blockage. Onset time is highly variable. It is theorized that the absence of symptoms or their intensity varies with such factors as strain of amoeba, immune health of the host, and associated bacteria and, perhaps, viruses. The amoeba's enzymes help it to penetrate and digest human tissues; it secretes toxic substances.

No extensive research is known to have been conducted heretofore to determine correlations and associations regarding the presence of pathogens in the gastrointestinal tract of individuals in, e.g., PDD, Parkinson's and Dysautonmia populations. Based on the findings described herein in accordance with the present invention, correlations and associations are found to exist between various disorders such as Autism, Parkinson's, ADD, ADHD and Dysautonomia, for example, and the presence of pathogens in an individual's digestive tract.

SUMMARY OF THE INVENTION

The present invention generally relates to methods for aiding in the diagnosis of disorders including, but not limited to, PDDs, Dysautonomic disorders, Parkinson's disease and SIDS. More particularly, the invention relates to a diagnosis method comprising analyzing a stool sample of an individual for the presence of a biological marker comprising one or more pathogens, which provides an indication of whether the individual has, or can develop, a disorder including, but not limited to, a PDD, Dysautonomia, Parkinson's disease and SIDS. In a preferred embodiment, a stool immunoassay is used to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

In another aspect of the invention, pathogens including, but not limited to, *Giardia, Cryptosporidium, E. histolytica, C. difficile*, Adenovirus, Rotavirus, and *H. pylori*, comprise biological markers whose presence in a stool sample, for example, are efficacious for determining whether an individual, especially a child, has, or can potentially develop, a disorder including, but not limited to, a PDD, Dysautonomia, Parkinsons disease, SID, and/or other neurological disorders.

These and other aspects, features, and advantages of the present invention will be described and become apparent from the following detailed description of preferred embodiments, which is to be read with the accompanying drawings.

BRIEF DESCRIPTION OF THE DRAWINGS

FIG. 1 is a table diagram illustrating various pathogens that tested positive in stool samples of individuals having a Dysautonomic disorder;

FIG. 2 is a table diagram illustrating various pathogens that tested positive in stool samples of individuals having Parkinson's, as compared with stool results of individuals not having Parkinson's disease;

FIG. 3 is a table diagram illustrating various pathogens that tested positive in stool samples of individuals having ADD or ADHD, as compared with stool results of individuals not having ADD or ADHD; and FIG. 4 is a table diagram illustrating various pathogens that tested positive in stool samples of individuals having a PDD.

DETAILED DESCRIPTION OF PREFERRED EMBODIMENTS

The present invention is directed to methods for aiding in the diagnosis of various human disorders, such as PDD, Dysautonomia, Parkinson's, SIDS, etc. In one aspect, a method comprises analyzing stool samples of an individual to determine the presence of pathogens including, but not limited to, *Giardia, Cryptosporidium, Entamoeba histolytica*, Adenovirus, Rotavirus, *H. pylori, Cyclospora, Microsoridia*, and/or *Isospora belli*. Preferably, the presence of one or more pathogens is determined using a stool immunoassay to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

In particular, a stool immunoassay results in the determination of the presence of a particular antigen (usually a protein) that the particular pathogen leaves behind (i.e., each microorganism is associated with a specific antigen). This antigen represents a pathogen, and is recognized by the gastrointestinal tract of the individual as a foreign protein. In accordance with one aspect of the invention, the presence of one or more antigens, regardless of the quantitative level, comprises a biological marker for determining if the person, especially a child, may either have or develop a disorder such as a PDD, Dysautonomia, Parkinson's, or SIDS.

Until now, there has been no known methods for analyzing stool samples to determine the presence of pathogens as biological markers to allow early diagnosis or screening of such disorders or conditions. It is postulated, for example, that the presence of antigen(s) and/or the microscopic presence of such organisms may signal the formation of a dysbiosis, and ultimately the formation of a malabsorption syndrome. This malabsorption syndrome can predispose the individual to the formation of a disorder such as autism, ADD, ADHD, SIDS, PDD, tourettes, OCD and other neurological conditions. In particular, the formation of malabsorption syndrome can affect, for instance, proper and essential protein digestion/absorption. And in the absence of proper protein digestion/absorption, the amino acids necessary for, e.g., the growth and development or normal functioning of certain chemical processes of individuals are absent.

Consequently, it is postulated, for example, that a lack of proper protein absorption, for instance, of an individual, especially children, can lead to various disorders such as autism, other PDDs, SIDS, and other disorders mentioned herein. Indeed, as described in each of the above-incorporated U.S. patent applications, abnormal protein digestion is found to occur in the PDD and dysautonomic populations. For instance, it was further determined that a sub-population of individuals suffering from ADD, ADHD and autism as well as a sub-population of those with dysautonomic conditions had an abnormal level of the enzyme chymotrypsin, indicated pancreatic insufficiency as a component of such disorders.

The following case studies indicate that there are correlations between the development of various disorders and the presence of microorganisms in an individual's digestive tract. It is to be understood that these examples are set forth by way of illustration only, and nothing therein shall be taken as a limitation upon the overall scope of the invention.
Case 1:

Stool sample were collected from two children diagnosed as having Familial Dysautonomia. The stool samples were analyzed for the presence of pathogens. As shown by the table in FIG. 1, the stool sample of Child 1 tested positive for *H. pylori, Giardia*, and *Cryptosporidium*. Further, the stool sample of Child 2 tested positive for *H. pylori, Giardia, Cryptosporidium* and Rotavirus.
Case 2:

Stool samples were collected from 15 individuals diagnosed as having Parkinson's disease. The stool samples were analyzed for the presence of pathogens. Further, stool samples were collected from an additional 15 individuals who were not diagnosed as having Parkinson's disease, nor having known familial association with Parkinson's or known GI conditions. These stool samples were also analyzed for the presence of pathogens.

The table in FIG. 2 illustrates the result of this study. As shown, the stools of each of the 15 individuals diagnosed as having Parkinson's disease tested positive for various pathogens including *H. pylori, Cryptosporidium, E. hystolytica, Giardia*, Rotavirus, *Camphylobacter*, and/or *C. difficile*. On the other hand, virtually all the stools of each of the 15 individuals not diagnosed as having Parkinson's disease tested negative for such pathogens.
Case 3:

Stool samples were collected from 13 children diagnosed as having either ADD or ADHD and analyzed for the presence of pathogens. Further, stool samples were collected from an additional 14 children not diagnosed as having ADD or ADHD and analyzed for the presence of pathogens.

The table in FIG. 3 illustrates the result of this study. As shown, the stools of each of the 13 children diagnosed as having either ADD or ADHD tested positive for various pathogens including as *H. pylori, Cryptosporidium, E. hystolytica, Giardia*, Rotavirus, *Camphylobacter*, and/or *C. difficile*. On the other hand, virtually all the stools of each of the 14 children not diagnosed as having ADD or ADHD tested negative for such pathogens.
Case 4:

Stool samples were collected from 19 children diagnosed as having Autism (via a CARS or ADOS test) and analyzed for the presence of pathogens. The results of this study are shown in FIG. 4. As shown, the stools of each of the 19 children diagnosed as having Autism tested positive for various pathogens including as *H. pylori, Cryptosporidium, E. hystolytica, Giardia*, Rotavirus, *Camphylobacter*, and/or *C. difficile*.

The results of these case studies indicate that there are correlations between the development of various disorders (such as Autism, Parkinson's, ADD and ADHD) and the presence of pathogens and/or corresponding antigens in an individual's digestive tract. It is postulated that these pathogens and/or corresponding antigens either promote gastrointestinal dysfunction or have some other direct or indirect effect on the individual, thereby causing such disorders. Further, it is possible that certain mechanisms associated with such disorders can be the cause of a proliferation of one or more pathogens in the gastrointestinal tract of an individual. Again, it is to be understood that nothing therein shall be taken as a limitation upon the overall scope of the invention.

For instance, although Case Study 4 involves Autism, based on the correlations described herein, it is believed that the present invention may be implemented for aiding in the diagnosis of other various PDDs such as Aspergers syndrome and other related disorders. Furthermore, although Case Study 1 involves Familial Dysautonomia, based on the correlations described herein, it is believed that the present invention may be implemented for aiding in the diagnosis of various dysautonomic disorders and dysautonomic conditions, including, but not limited to, Familial Dysautonomia (or Riley-Day Syndrome), Guillaine-Barre Syndrome (GBS) (acute idiopathic polyneuropathy), fetal fatal insomnia (FFI), diabetic cardiovascular neuropathy, Hereditary Sensory and autonomic neuropathy type III (HSAN III), central autonomic disorders including multiple system atrophy (Shy-Drager syndrome), orthostatic intolerance syndrome including mitral value prolapse, postural tachycardia syndrome (POTS), and idiopathic hypovolemia, dysautonomic syndromes and disorders of the catecholemine family including baroreflex failure, dopamine-B-Hydroxylase deficiency, pheochromocytoma, chemodectina, familial paraganglioma syndrome, tetrahydrobiopterin deficiency, aromatic-L-amino acid decarboxylase deficiency, Menke's disease, monoamine oxidase deficiency states, and other disorders of dopamine metabolism, dysautonomic syndromes and disorders of the cardiovasular system, Chaga's disease, Diabetic autonomic failure, pure autonomic failure, syncope, hypertension, cardiovascular disease, renal disease and SIDS. Further, the present invention is believed to be efficacious for diagnosing other neurological disorders such as OCD (obsessive compulsive disorder) and Tourette's syndrome.

In summary, a method according to the present invention for aiding in the diagnosis of a disorder comprises analyzing stool samples of an individual to determine the presence of one or more pathogens including, but not limited to, *H. pylori, Cryptosporidium, Entamoeba histolytica, Giardia*, Rotavirus, *Camphylobacter*, and/or *C. difficile*. Other pathogens that may be analyzed include, for example, Adenovirus, *Cyclospora, Microsoridia*, and/or *isospora belli*. In a preferred embodiment, the presence of one or more pathogens is determined by a stool immunoassay to determine the presence of associated antigens. The presence of one or more pathogens comprises a biological marker for determining if an individual, especially a child, may either have or develop a disorder, including, but not limited to, PDD (such as Autism), Dysautonomia (or other dysautonomic conditions), Parkinson's disease, SIDS, or other dysautonomic and/or neurological disorders.

Although illustrative embodiments have been described herein with reference to the accompanying drawings, it is to be understood that the present invention is not limited to those precise embodiments, and that various other changes and modifications may be to effected therein by one skilled in the art without departing from the scope or spirit of the invention. All such changes and modifications are intended to be included within the scope of the invention as defined by the appended claims.

What is claimed is:

1. A method for determining if an individual has, or can develop, Attention Deficit Disorder (ADD) or Attention Deficit Hyperactive Disorder (ADHD), comprising the steps of:
    analyzing a stool sample obtained from the individual with a stool immunoassay for the presence or absence an antigen associated with a pathogen, wherein the pathogen comprises *Helicobacter pylori, Cryptosporidium, Entamoeba histolytica, Giardia*, Rotavirus, *Camphylobacter* or *Clostridium difficile;*
    detecting the level of chymotrypsin present in the stool sample, wherein the presence of the antigen and an abnormally low level of chymotrypsin in the stool sample allow for a determination that the individual has, or can develop, ADD or ADHD.

2. The method of claim 1, wherein the presence of the pathogen in the stool sample is determined using stool immunoassay.

3. The method of claim 1, wherein the pathogen comprises *Helicobacter pylori*.

4. The method of claim 1, wherein the pathogen comprises *Clostridium difficile*.

5. The method of claim 1, wherein the pathogen comprises *Cryptosporidium*.

6. The method of claim 1, wherein the pathogen comprises *Giardia*.

7. The method of claim 1, wherein the pathogen comprises Rotavirus or Adenovirus.

8. The method of claim 1, wherein the pathogen comprises *Entamoeba histolytica*.

\* \* \* \* \*

UNITED STATES PATENT AND TRADEMARK OFFICE
CERTIFICATE OF CORRECTION

| | | |
|---|---|---|
| PATENT NO. | : 8,921,054 B2 | Page 1 of 1 |
| APPLICATION NO. | : 14/037652 | |
| DATED | : December 30, 2014 | |
| INVENTOR(S) | : Joan M. Fallon | |

It is certified that error appears in the above-identified patent and that said Letters Patent is hereby corrected as shown below:

In the Claims

Column 8, line 6, in Claim 1, please delete "presence or absence an" and replace with --presence of absence of an--.

Signed and Sealed this
Fourteenth Day of April, 2015

Michelle K. Lee
*Director of the United States Patent and Trademark Office*